(12) United States Patent
Nambu

(10) Patent No.: US 12,302,868 B2
(45) Date of Patent: May 20, 2025

(54) CHICK PRODUCTION METHOD AND CHICK PRODUCTION SYSTEM

(71) Applicant: NABEL CO., LTD., Kyoto (JP)

(72) Inventor: Kunio Nambu, Kyoto (JP)

(73) Assignee: NABEL CO., LTD., Kyoto (JP)

( * ) Notice: Subject to any disclaimer, the term of this patent is extended or adjusted under 35 U.S.C. 154(b) by 0 days.

(21) Appl. No.: 18/001,212

(22) PCT Filed: Jun. 11, 2021

(86) PCT No.: PCT/JP2021/022334
§ 371 (c)(1),
(2) Date: Dec. 8, 2022

(87) PCT Pub. No.: WO2021/251490
PCT Pub. Date: Dec. 16, 2021

(65) Prior Publication Data
US 2023/0217904 A1    Jul. 13, 2023

(30) Foreign Application Priority Data

Jun. 12, 2020 (JP) ................................. 2020-101958

(51) Int. Cl.
*A01K 43/00* (2006.01)
*A01K 41/02* (2006.01)
(Continued)

(52) U.S. Cl.
CPC .......... *A01K 43/00* (2013.01); *A01K 41/023* (2013.01); *A01K 43/06* (2013.01); *A01K 43/08* (2013.01); *G01N 33/02* (2013.01)

(58) Field of Classification Search
CPC ........ A01K 43/00; A01K 43/06; A01K 43/08; A01K 41/023
See application file for complete search history.

(56) References Cited

U.S. PATENT DOCUMENTS

| 2013/0319335 A1 | 12/2013 | Hebrank et al. |
| 2016/0050891 A1 | 2/2016 | Phelps et al. |

(Continued)

FOREIGN PATENT DOCUMENTS

| EP | 2 377 393 A1 | 10/2011 | |
| EP | 2845477 A1 * | 3/2015 | ............. A01K 43/00 |

(Continued)

OTHER PUBLICATIONS

Google Patent Translation of RU 2703304 (Year: 2015).*

(Continued)

*Primary Examiner* — Monica L Perry
*Assistant Examiner* — Aaron M Rodziwicz
(74) *Attorney, Agent, or Firm* — Studebaker Brackett PLLC

(57) ABSTRACT

A new chick production method and a new chick production system are obtained which are different from a conventional method in which all live eggs are collectively accommodated in a hatcher tray to develop chicks. The chick production method of the present invention divides mid-hatch eggs into a plurality of groups based on physical information measured for the mid-hatch eggs during a period from when the eggs are accommodated in a setter tray to when the eggs are transferred to a hatcher tray, and accommodates the mid-hatch eggs in the hatcher tray to develop chicks. In addition, a chick production system of the present invention includes a measurement unit, a sorting unit, and an accommodation unit, and the chicks are developed by each of a plurality of hatcher trays.

12 Claims, 5 Drawing Sheets

(51) Int. Cl.
A01K 43/06 (2006.01)
A01K 43/08 (2006.01)
G01N 33/02 (2006.01)

(56) References Cited

U.S. PATENT DOCUMENTS

| | | |
|---|---|---|
| 2018/0199551 A1 | 7/2018 | Meter |
| 2018/0220626 A1 | 8/2018 | Williams |
| 2020/0163314 A1* | 5/2020 | Gabbai .................... G06N 3/08 |
| 2020/0375152 A1* | 12/2020 | Van De Loo ........ B25J 15/0625 |

FOREIGN PATENT DOCUMENTS

| | | | | |
|---|---|---|---|---|
| JP | 2011106892 A * | 6/2011 | ............. | A01K 43/00 |
| JP | 2019-502396 A | 1/2019 | | |
| JP | 2019-505207 A | 2/2019 | | |
| RU | 2703304 C9 * | 2/2020 | ............. | A01K 43/00 |
| WO | WO-2014199773 A1 * | 12/2014 | ............. | A01K 43/00 |
| WO | 2017/125596 A1 | 7/2017 | | |
| WO | 2017/127377 A1 | 7/2017 | | |
| WO | WO-2017195128 A1 * | 11/2017 | ............. | A01K 1/015 |
| WO | 2018/101139 A1 | 6/2018 | | |
| WO | WO-2018148115 A1 * | 8/2018 | ............. | A01K 41/06 |
| WO | 2019/007521 A1 | 1/2019 | | |
| WO | WO-2019007741 A1 * | 1/2019 | ........... | A01K 31/165 |

OTHER PUBLICATIONS

Translation of RU2703304 (Year: 2015).*
International Search Report issued in PCT/JP2021/022334; mailed Jul. 27, 2021.
The extended European search report issued by the European Patent Office on Feb. 23, 2024, which corresponds to European Patenf Application No. 21821232.2-1105 and is related to U.S. Appl. No. 18/001,212.

* cited by examiner

CHICK PRODUCTION METHOD AND CHICK PRODUCTION SYSTEM

TECHNICAL FIELD

The present invention relates to a chick production method and a chick production system.

BACKGROUND ART

Eggs used for production of chicks are incubated under an environment of a predetermined temperature, humidity, or the like, and an inspection is performed to determine an activity situation of the embryo inside the egg, namely, life and death or the like during the incubation. The eggs determined to be non-live (for example, unfertilized eggs, spoiled eggs, and intermediately dead eggs) by the inspection are removed as appropriate (for example, see Japanese National Patent Publication No. 2019-505207 (PTL 1)) because the hatching is not required to be continued. That is, in the conventional method, the eggs are grouped by two options of whether the eggs are live at the time of the inspection, and the incubation of the group of live eggs is continued, and the incubation of the other groups is interrupted.

In the group in which the incubation of eggs is continued, for example, eggs are accommodated in a hatcher tray as illustrated in Japanese National Patent Publication No. 2019-502396 (PTL 2) to develop chicks. All the eggs placed in one hatcher tray do not develop the chicks at the same time. There is a difference in the timing at which the chicks are developed for each egg, and a term "hatch window" is used to represent the time interval from the development of the first chick to the development of the last chick. When the hatch window becomes wider, a difference in growth is widened between the chicks developed at the beginning and the chicks developed at the end. For this reason, the hatch window is required to be narrowed as much as possible.

CITATION LIST

Patent Literature

PTL 1: Japanese National Patent Publication No. 2019-505207
PTL 2: Japanese National Patent Publication No. 2019-502396

SUMMARY OF INVENTION

Technical Problem

The inventor has focused on the fact that a difference in a state and a characteristic of the embryo is found at an intermediate stage of the incubation among the groups determined as the live eggs at the time of the inspection. An object of the present invention is to provide a new chick production method and a new chick production system that are different from the conventional method in which the chicks are developed by collectively accommodating all the live eggs in the hatcher tray.

Solution to Problem

A chick production method according to the present invention divides mid-hatch eggs into a plurality of groups based on physical information measured for the mid-hatch eggs during a period from when the mid-hatch eggs are accommodated in a setter tray to when the mid-hatch eggs are transferred to a hatcher tray, and accommodates the mid-hatch eggs in the hatcher tray for each group to develop chicks.

A chick production method according to the present invention includes a measurement process, an accommodation process, and a chick development process. In the measurement process, the physical information about the mid-hatch eggs is measured during the period from when the mid-hatch eggs are accommodated in the setter tray to when the mid-hatch eggs are transferred to the hatcher tray. In the accommodation process, the mid-hatch eggs are divided into the plurality of groups based on the measured physical information, and accommodated in the hatcher tray. In the chick development process, temperature of the mid-hatch eggs accommodated in the hatcher tray is adjusted to develop the chicks.

Here, the "physical information" varies depending on eggs even when the eggs are of the same lot, and can be measured using the measurement unit. Examples of the physical information include a weight of an egg, an eggshell temperature, an ovoid coefficient (obtained by dividing a minor axis of the egg by a major axis and multiplying the major axis by 100), an air chamber height, an air chamber volume, an eggshell thickness, an eggshell strength, and fetal movement and a heartbeat of an embryo.

When the mid-hatch eggs are divided into the plurality of groups, attribute information about the mid-hatch eggs may be used in addition to physical information about the mid-hatch eggs.

At this point, the "attribute information" is common to the eggs of the same lot. Examples of the attribute information include a chicken species, age of a parent chicken, a laying date and time, a content of feed, a medical history and a vaccination history of the parent chicken.

A chick development system of the present invention includes a measurement unit, a sorting unit, and an accommodation unit, and chicks are developed from mid-hatch eggs in each of a plurality of hatcher trays. The measurement unit measures physical information about mid-hatch egg accommodated in a setter tray or the mid-hatch egg taken out from the setter tray. The sorting unit divides the mid-hatch eggs into a plurality of groups based on the physical information measured by the measurement unit. The accommodation unit accommodates the mid-hatch eggs in a plurality of hatcher trays for each group divided by the sorting unit.

Advantageous Effects of Invention

According to the present invention, the new chick production method and new chick production system can be provided which are different from the conventional method in which all the live eggs are collectively accommodated in the hatcher tray to develop the chicks.

The foregoing and other objects, features, aspects and advantages of the present invention will become more apparent from the following detailed description of the present invention when taken in conjunction with the accompanying drawings.

DESCRIPTION OF EMBODIMENT

With reference to FIGS. 1 to 4, an embodiment of the present invention will be described in detail below.

Figure 1:
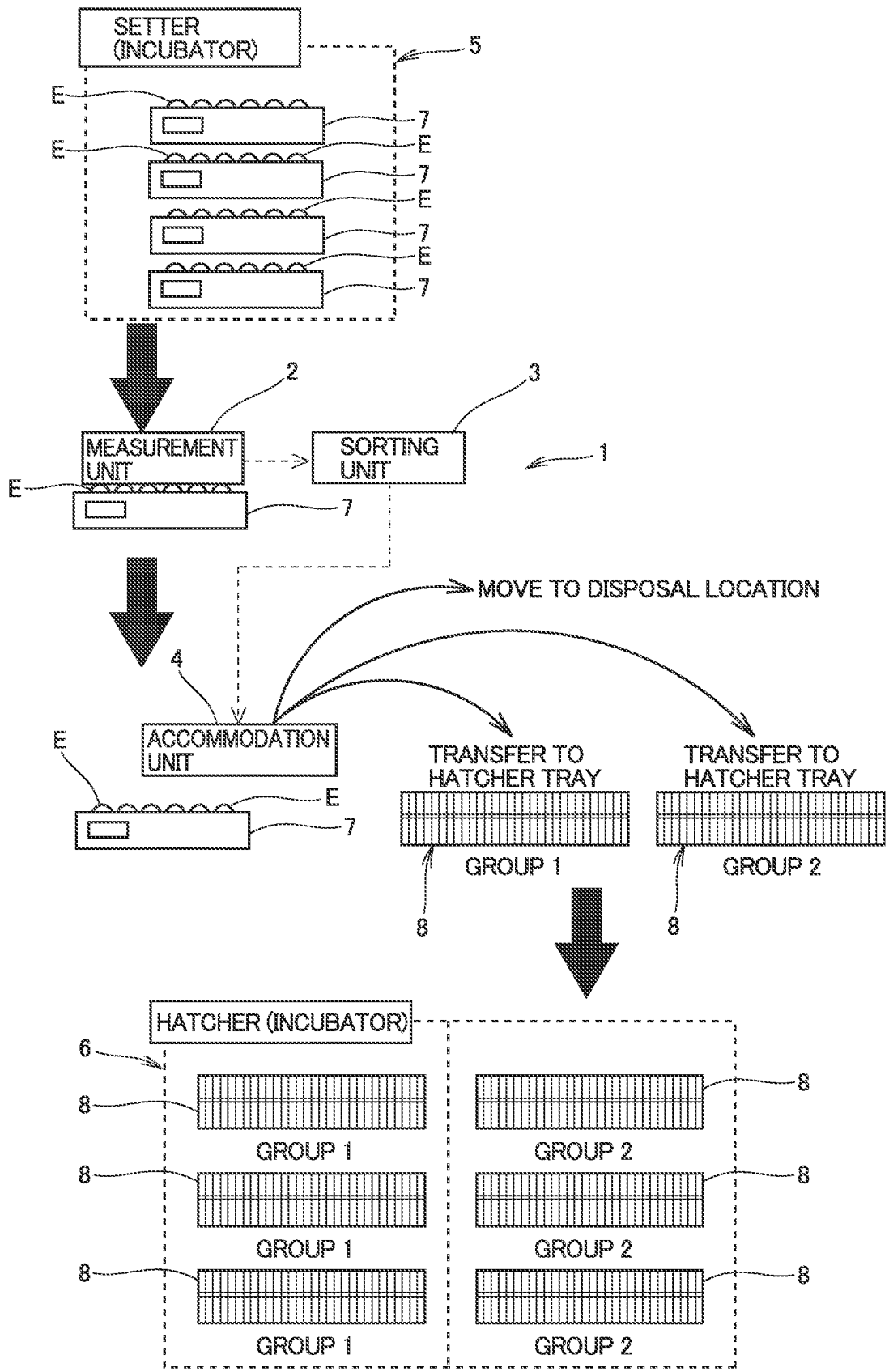
FIG. 1 is a view illustrating a chick production system according to an embodiment of the present invention.
Figure 2:
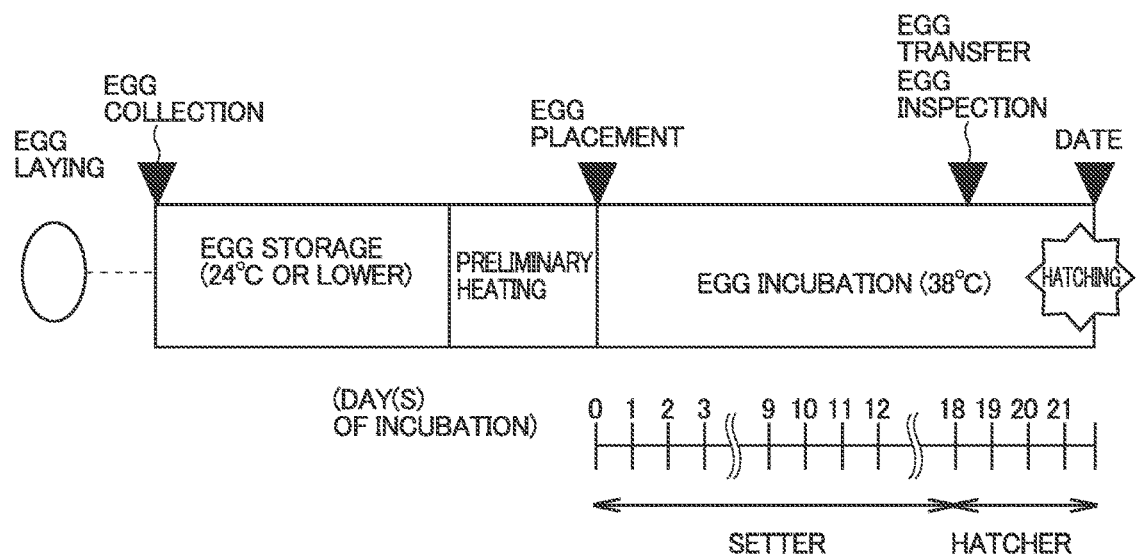
FIG. 2 is a view illustrating a chick production process in a general hatchery.
Figure 3:
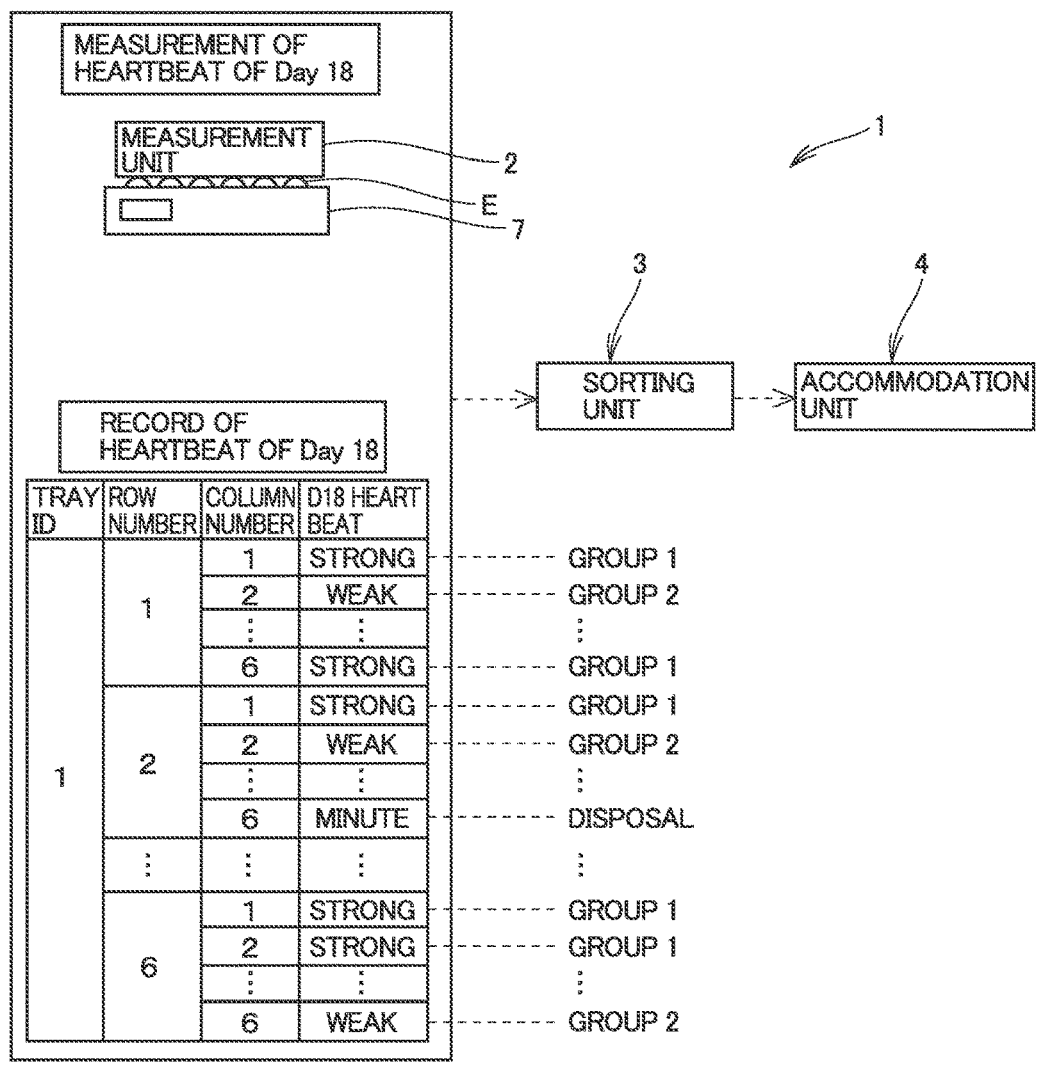
FIG. 3 is a view illustrating a specific example of the chick production system of the embodiment.

In a breeder company, a farm where a group of breeding hens which are parents of layer chickens is bred is called a breeder farm. Eggs laid in this breeder farm are once collected in an egg storage location as illustrated in FIG. 2. Thereafter, the eggs are subjected to a process called preliminary heating. Thereafter, the eggs are placed in an incubator (hereinafter, referred to as a "setter 5") to start incubation. On the 18th day or the 19th day from entering setter 5, the eggs are transferred to an incubator (hereinafter, referred to as "hatcher 6"). Thereafter, chicks are developed on about the 21st day from the start of the incubation (egg placement).

A setter tray 7 (also called a "flat") capable of individually accommodating the eggs and maintaining the eggs upright is used in setter 5. On the other hand, in hatcher 6, an open hatcher tray 8 (also called a "basket") in which the eggs are not individually accommodated is used such that the eggs can hatch at any time.

In this incubation process, when the eggs are transferred from setter tray 7 to hatcher tray 8, operation dividing the eggs into live eggs and non-live eggs is usually performed.

A chick production system 1 of the embodiment further groups the live eggs to produce the chicks for each group. Chick production system 1 includes a measurement unit 2, a sorting unit 3, and an accommodation unit 4. Hereinafter, the Xth day after the egg is put in setter 5 is referred to as the "Xth day after the incubation". The egg from when it is put in setter 5 until when the chick is developed is referred to as a "mid-hatch egg E".

Measurement unit 2 measures physical information about mid-hatch egg E taken out from setter tray 7. Measurement unit 2 measures the physical information at timing when mid-hatch egg E is transferred from setter tray 7 to hatcher tray 8, for example, on the 18th day from the incubation. Measurement unit 2 may measure the physical information about mid-hatch eggs E while mid-hatch eggs E are accommodated in setter trays 7, or measure the physical information about mid-hatch eggs E while mid-hatch eggs E are taken out from setter trays 7. For example, the physical information is information about a heartbeat of an embryo of mid-hatch egg E (hereinafter, referred to as "heartbeat data"). The heartbeat data includes a heart rate and a heartbeat intensity. For example, measurement unit 2 includes an irradiation portion and a light receiving portion (both not illustrated). For example, measurement unit 2 detects light (transmitted light) transmitted through the egg in light irradiated to the egg from the irradiation portion by the light receiving portion. For example, measurement unit 2 obtains the physical information using a change in the intensity of the transmitted light detected by the light receiving portion. As measurement unit 2, one well-known in this field can be used.

Sorting unit 3 divides mid-hatch eggs E into a plurality of groups based on the physical information measured by measurement unit 2. For example, sorting unit 3 estimates a state and a characteristic of the embryo of mid-hatch egg E based on the physical information measured by measurement unit 2. Sorting unit 3 further sorts mid-hatch eggs E into a group 1 of the live eggs, a group 2 of the live eggs, and a group of non-live eggs by, for example, comparing the estimated characteristic of the embryo with a predetermined threshold. For example, group 1 is a group of mid-hatch eggs E that are estimated to hatch at relatively early timing. Group 2 is a group of mid-hatch eggs E that are estimated to hatch at relatively late timing. Sorting unit 3 estimates the hatching timing of mid-hatch egg E using, for example, the heartbeat data of target mid-hatch egg E on the 18th day of the incubation. Specifically, when the heartbeat data is clear and stable (indicated by "strong" in FIG. 3), it can be estimated that the hatching timing of the eggs will be relatively early. On the other hand, when the heartbeat data is not stable (indicated by "weak" in FIG. 3), it can be estimated that the hatching timing of the eggs will be relatively late. When the heartbeat data is unclear (illustrated as "minute" in FIG. 3), it can be estimated that the eggs will not hatch.

When the heartbeat data estimating the hatching timing is measured, the heartbeat data may be measured on days other than the 18th day of the incubation, for example, the 11th day to the 14th days of the incubation. The Embryo with the later hatching timing (developed at a relatively later stage) have the lower heart rate and the lower heartbeat intensity throughout the incubation period compared with the embryo with the earlier hatching timing (developed at a relatively earlier stage).

Accommodation unit 4 accommodates mid-hatch eggs E in a plurality of hatcher trays 8 for each group divided by sorting unit 3. For example, accommodation unit 4 is a device that transfers mid-hatch egg E. Accommodation unit 4 transfers group 1 of live eggs to hatcher tray 8 of group 1, transfers group 2 of live eggs to another hatcher tray 8, and moves non-live eggs to a disposal location. Accommodation unit 4 is a device that transfers mid-hatch eggs E from setter tray 7 to hatcher tray 8, and can hold or release mid-hatch eggs E one by one.

Figure 4:
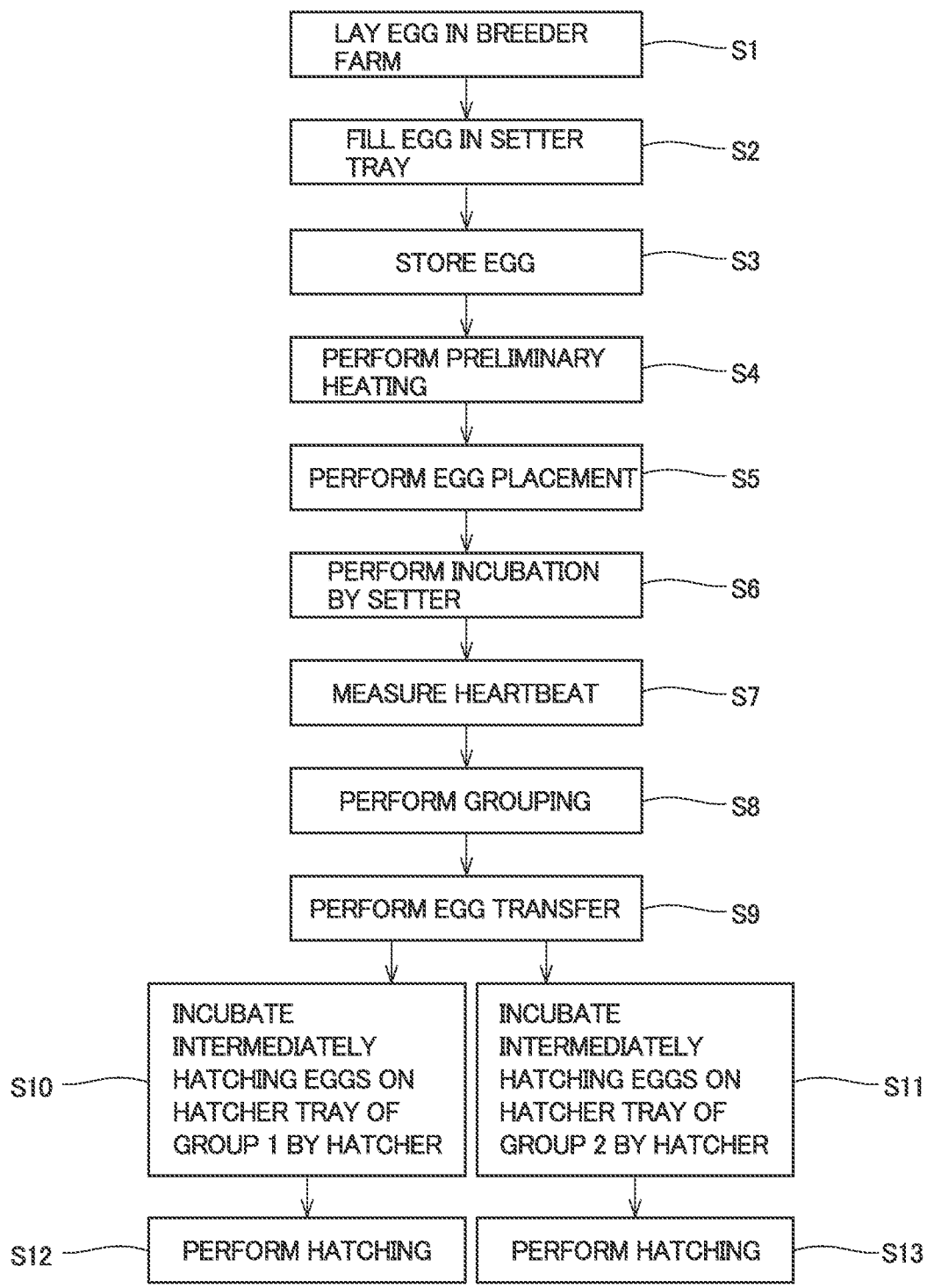
FIG. 4 is a flowchart illustrating a chick production method of the embodiment.

With reference to FIG. 4, an example of the chick production method will be described below.

The eggs laid in the breederfarm (step S1) are filled in setter tray 7 (step S2), and temporarily stored (step S3). After the preliminary heating (step S4), the eggs are put in setter 5 (step S5), and the temperature is adjusted for a predetermined period (step S6).

On the 18th day (or 19th day) after being put in setter 5, setter tray 7 containing mid-hatch eggs E is taken out from setter 5, and measurement unit 2 measures the heartbeat data of mid-hatch eggs E (step S7). Sorting unit 3 estimates the state and characteristic of mid-hatch eggs E based on the heartbeat data obtained in step S7, and groups mid-hatch eggs E (step S8). Accommodation unit 4 takes out mid-hatch egg E from setter tray 7. Accommodation unit 4 moves mid-hatch egg E to hatcher tray 8 based on the group divided in step S8 (step S9).

Hatcher trays 8 in group 1 and mid-hatch eggs E of hatcher trays 8 in group 2 are further temperature-adjusted for a predetermined period in hatcher 6 (steps S10, S11). Hatcher tray 8 of group 1 and hatcher tray 8 of group 2 are separately placed in hatcher 6. Different environmental control may be performed in hatcher 6 for hatcher tray 8 of group 1 and hatcher tray 8 of group 2. Thus, deviation of hatch windows of group 1 and group 2 can also be adjusted, and the chicks with uniform quality can be supplied.

Thereafter, the chicks are developed in each of hatcher tray 8 group 1 and hatcher tray 8 of group 2 (steps S12, S13). Many of the chicks hatching in hatcher tray 8 of group 1 hatch earlier as a whole than the chicks hatching in hatcher tray 8 of group 2. That is, homogenization of hatching timing (also referred to as development timing) can be devised for each hatcher tray 8.

As described above, the chick production method of the embodiment divides mid-hatch eggs E into the plurality of groups based on the physical information measured for mid-hatch eggs E during a period from when the eggs are accommodated in setter tray 7 to when the eggs are transferred to hatcher tray 8, and accommodates mid-hatch eggs E in hatcher tray 8 to develop the chicks. From a different point of view, the chick production method of the present invention includes a measurement process (step S7), an accommodation process (step S9), and a chick development process (steps S10 to S13). In the measurement process (step S7), the physical information about mid-hatch eggs E is measured during the period from when mid-hatch eggs E are accommodated in setter trays 7 to when mid-hatch eggs E are transferred to hatcher trays 8. In the accommodation process (step S9), mid-hatch eggs E are divided into the plurality of groups based on the measured physical information, and are accommodated in hatcher tray 8. In the chick development process (steps S10 to S13), the temperature of mid-hatch egg E accommodated in hatcher tray 8 is adjusted to develop the chick.

In addition, measurement unit 2, sorting unit 3, and accommodation unit 4 are included as production system 1 implementing such the chick production method, and the chicks are developed in each of the plurality of hatcher trays 8. Measurement unit 2 measures physical information about mid-hatch egg E accommodated in setter tray 7 or mid-hatch egg E taken out from setter tray 7. Sorting unit 3 divides mid-hatch eggs E into a plurality of groups based on the physical information measured by measurement unit 2. Accommodation unit 4 accommodates mid-hatch eggs E in the plurality of hatcher trays 8 for each group divided by sorting unit 3. With such the configuration, the homogenization of the development timing can be devised for each of hatcher trays 8.

The physical information is information measured at the time when mid-hatch eggs E are transferred from setter tray 7 to hatcher tray 8, so that mid-hatch eggs E can be grouped based on the state and characteristic of the embryo at the timing closer to the hatching.

The present invention is not limited to the above-described embodiment.

Figure 5:
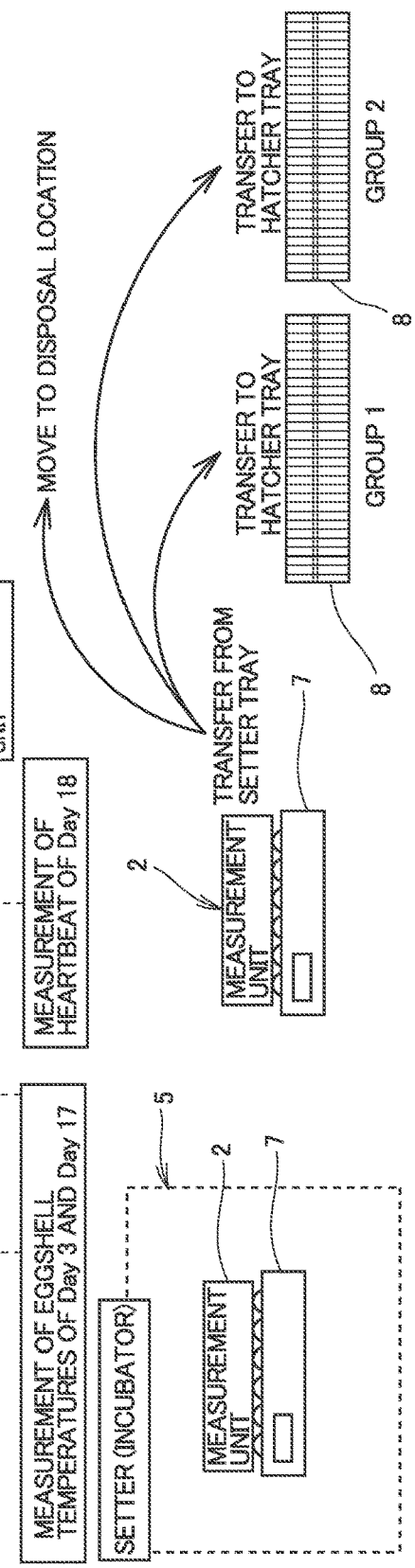
FIG. 5 is a view illustrating a chick production system according to a modification of the present invention.
Figure 6:
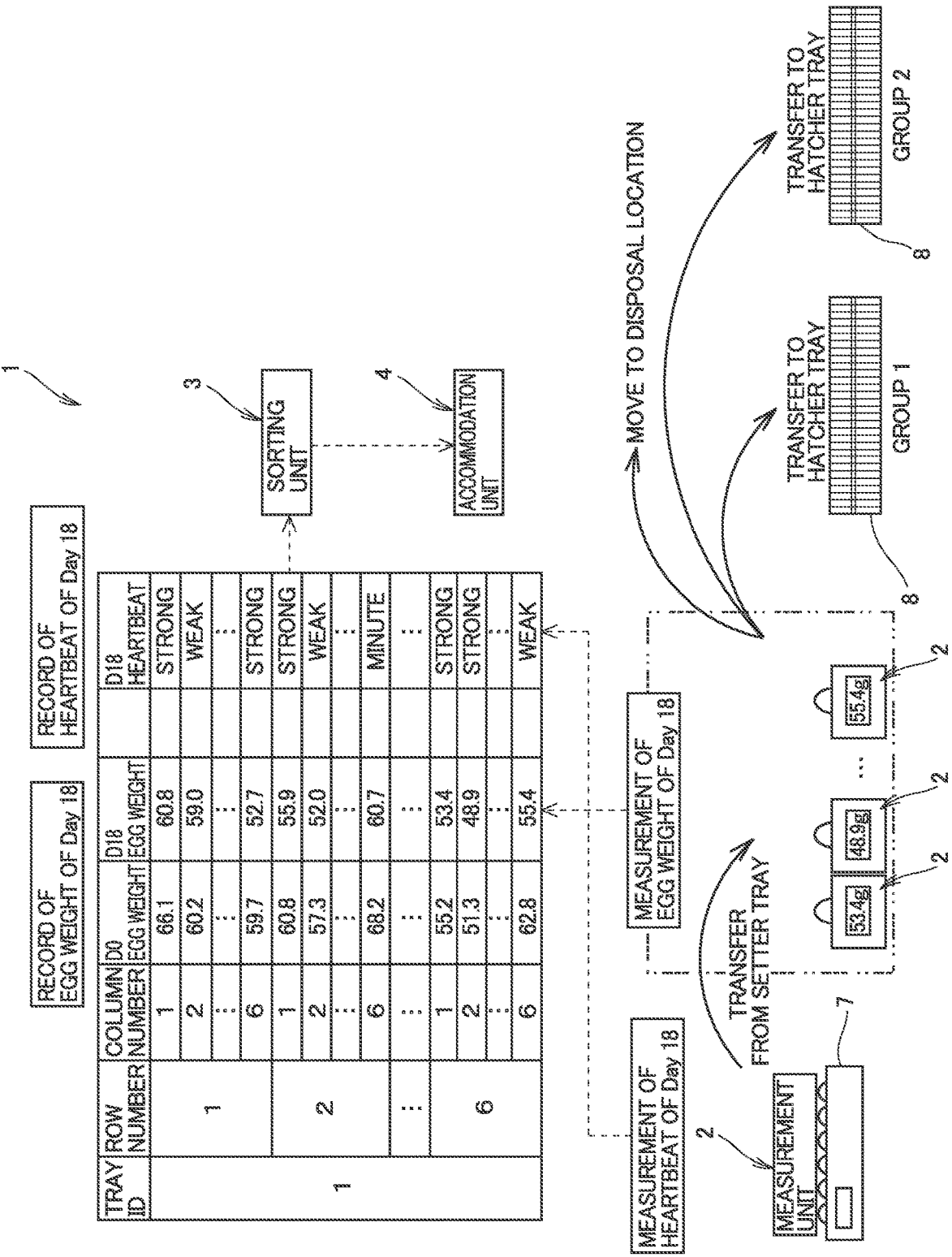
FIG. 6 is a view illustrating a chick production system according to another modification of the present invention.

Each of FIGS. 5 and 6 illustrates chick production system 1 according to a modification. In each modification, the same reference numerals are given to the same (or equivalent) parts as those of the above-described embodiment, and the description thereof will not be repeated unless necessary.

Chick production system 1 in FIG. 5 uses information about the eggshell temperature as the physical information. Measurement unit 2 measures the eggshell temperature as the physical information while the egg is accommodated in setter tray 7. For example, measurement unit 2 measures the eggshell temperature at the third day of the incubation and the 17th day of the incubation. When mid-hatch eggs E are divided into the plurality of groups, sorting unit 3 uses a change in a plurality of pieces of physical information (eggshell temperatures) measured on different days (for example, the third day of the incubation and the 17th day of the incubation) for one mid-hatch egg E. It is generally known that the embryo generates heat from around the 12th or 13th day from the start of the incubation to rise an eggshell temperature. By utilizing this characteristic, the timing at which measurement unit 2 measures the eggshell temperature is not limited to the third day of the incubation and the 17th day of the incubation.

That is, the chick production method using chick production system 1 in FIG. 5 is basically similar to the chick production method in FIG. 4, but contents of steps S7 and S8 in FIG. 4 are different from the chick production method in FIG. 4. The details will be described below.

In the chick production method using chick production system 1 in FIG. 5, after the processes from steps S1 to S6 in FIG. 4 are performed, as step S7 that is the process of measuring physical information, the eggshell temperature as an example of the physical information is measured on each of different days for one mid-hatch egg E. For example, the day on which the measurement is performed can be the third day of the incubation and the 17th day of the incubation as described above. Furthermore, as step S7 that is the process of measuring the physical information, the heartbeat data of mid-hatch egg E is measured by measurement unit 2 on the 18th day of the incubation (or the 19th day of the incubation) similarly to the chick production method in FIG. 4. The measurement of the eggshell temperature and the heartbeat data is performed while mid-hatch egg E is accommodated in setter tray 7. The measurement of the eggshell temperature is performed while setter tray 7 is accommodated in setter 5. The heartbeat data is measured while setter tray 7 is removed from setter 5.

Thereafter, steps S8 and S9 are performed as the process of dividing mid-hatch eggs E into the plurality of groups to accommodate the groups in hatcher tray 8. The change in the eggshell temperature, which is the change in the plurality of pieces of physical information measured for one mid-hatch egg E, is used in step S8. In step S8, mid-hatch eggs E may be grouped using both the heartbeat data and the change in the eggshell temperature, but only the change in the eggshell temperature may be used. Alternatively, the heartbeat data may be used for distinguishing between the live egg and the non-live egg for mid-hatch egg E. The change in the eggshell temperature and the heartbeat data may be used for grouping the live eggs, or only the change in the eggshell temperature may be used.

Thereafter, the chicks can be developed by performing steps S10 to S13 in FIG. 4.

In addition, chick production system 1 in FIG. 6 uses information about an egg weight as the physical information. Measurement unit 2 measures the egg weight as the physical information at the time when the mid-hatch eggs are transferred to setter tray 7 or at the time when the mid-hatch eggs are transferred from setter tray 7 to hatcher tray 8. For example, measurement unit 2 measures the egg weight on the 0th day of the incubation and the 18th day of the incubation. When classifying mid-hatch eggs E into the plurality of groups, sorting unit 3 uses the change in the plurality of pieces of physical information (egg weights) measured on different days (for example, the 0th day of the incubation and the 18th day of the incubation) for one mid-hatch egg E. It is known that the egg weight usually decreases by about 12% to about 13% at around the 18th day of the incubation as compared with the egg weight at the start of the incubation. By using this characteristic, the timing at which measurement unit 2 measures the egg weight is not limited to the 0th day of the incubation and the 18th day of the incubation.

That is, the chick production method using chick production system 1 in FIG. 6 is basically similar to the chick production method in FIG. 4, but contents of steps S7 and S8 in FIG. 4 are different from the chick production method in FIG. 4. The details will be described below.

In the chick production method using chick production system 1 in FIG. 6, as step S7 that is the process of measuring the physical information, the egg weight as an example of the physical information is measured for one mid-hatch egg E on each of different days. For example, the day on which the measurement is performed can be the 0th day of the incubation and the 18th day of the incubation as described above. The measurement of the egg weight on the 0th day of the incubation is performed when mid-hatch eggs E are accommodated in setter tray 7. The measurement of the egg weight on the 18th day of the incubation is performed when mid-hatch eggs E are transferred from setter tray 7 to hatcher tray 8. Furthermore, as step S7 that is the process of measuring the physical information, the heartbeat data of mid-hatch egg E is measured by measurement unit 2 on the 18th day of the incubation (or the 19th day of the incubation) similarly to the chick production method in FIG. 4. The heartbeat data is measured while mid-hatch egg E is accommodated in setter tray 7.

Thereafter, steps S8 and S9 are performed as the process of dividing mid-hatch eggs E into the plurality of groups to accommodate the groups in hatcher tray 8. The change in the egg weight, which is the change in the plurality of pieces of physical information measured for one mid-hatch egg E, is used in step S8. In step S8, grouping of mid-hatch eggs E may be performed using both the heartbeat data and the change in the egg weight, but only the change in the egg weight may be used. Alternatively, the heartbeat data may be used for distinguishing between the live egg and the non-live egg for mid-hatch egg E. The change in the egg weight and the heartbeat data may be used for grouping the live eggs, or only the change in the egg weight may be used.

Thereafter, the chicks can be developed by performing steps S10 to S13 in FIG. 4.

The effects according to the above-described embodiment can be obtained with the chick production system and the chick production method as illustrated in FIGS. 5 and 6. Furthermore, using the information about the eggshell temperature and the egg weight as the physical information, the accuracy of the homogenization of the development timing can be improved or mid-hatch eggs E according to the states and characteristics (normal chicks, chicks with abnormality, or males and females, and the like) of other embryos can be grouped.

As another modification, when mid-hatch eggs E are divided into the plurality of groups (in steps S8 and S9, the hatching eggs are divided into the plurality of groups and accommodated in hatcher tray 8), attribute information about mid-hatch eggs E may be used in addition to the physical information about mid-hatch eggs E. Examples of the attribute information include a chicken species, age of a parent chicken, a laying date and time, a content of feed, and a medical history and a vaccination history of the parent chicken.

Examples of the physical information include the weight of the egg (egg weight), the eggshell temperature, an ovoid coefficient (obtained by dividing a minor axis of the egg by a major axis and multiplying the major axis by 100), an air chamber height, an air chamber volume, an eggshell thickness, an eggshell strength, and fetal movement and the heartbeat of the embryo. Even when information about the heartbeat is used as the physical information, the measurement timing of the information is not limited to the 18th day of the incubation. In addition, the purpose of grouping is not limited to the homogenization of the development timing (narrowing of the hatch window).

When mid-hatch eggs E are divided into the plurality of groups, sorting unit 3 may use the change in the plurality of pieces of physical information measured on different days for one mid-hatch egg E, or use only one piece of physical information measured at one time point of one mid-hatch egg E. Sorting unit 3 may group mid-hatch eggs E using only one type (for example, only the heartbeat data, only the eggshell temperature, only the egg weight) of measured values of the physical information, or group mid-hatch eggs E using a plurality of types of measured values in combination.

Measurement unit 2 may measure the physical information about mid-hatch egg E in setter 5, or measure the physical information about mid-hatch egg E after being taken out from setter 5. Measurement unit 2 may measure the physical information about mid-hatch egg E using an image.

The above embodiment is only by way of example, and the present disclosure is not limited to the above embodiment. The scope of the present invention is defined by not the above description, but the claims, and it is intended that all modifications within the meaning and scope of the claims are included in the present invention.

INDUSTRIAL APPLICABILITY

The present invention can be used for a method for selecting the mid-hatch eggs, the chick production method, a system for selecting the mid-hatch eggs, and the chick production system.

REFERENCE SIGNS LIST

1: chick production system, 2: measurement unit, 3: sorting unit, 4: accommodation unit, 5: setter, 6: hatcher, 7: setter tray, 8: hatcher tray, E: mid-hatch egg

The invention claimed is:

1. A chick production method comprising:
measuring, by a measuring device, physical information about mid-hatch eggs during a period from when the mid-hatch eggs are accommodated in a setter tray to when the mid-hatch eggs are transferred to a hatcher tray;
dividing, by a sorter, the mid-hatch eggs into a plurality of groups based on the measured physical information to accommodate the mid-hatch eggs in the hatcher tray;
adjusting, by a hatcher, temperature of the mid-hatch eggs accommodated in the hatcher tray to develop chicks,
wherein the plurality of groups include a first live group, a second live group, and a non-live group, wherein the first live group has a first characteristic different from a second characteristic of the second live group; and
performing, by the hatcher, different temperature control in the hatcher for the first live group and for the second live group.

2. The chick production method according to claim 1, wherein, in the dividing the mid-hatch eggs into the plurality of groups to accommodate the mid-hatch eggs in the hatcher tray, attribute information about the mid-hatch eggs is used in addition to the physical information about the mid-hatch eggs.

3. The chick production method according to claim 1, wherein, in the measuring the physical information, the physical information is measured on each of different days for one of the mid-hatch eggs, and in the dividing the mid-hatch eggs into the plurality of groups to accommodate the mid-hatch eggs in the hatcher tray, a change in a plurality of pieces of the physical information measured for one of the mid-hatch eggs is used.

4. The chick production method according to claim 1, wherein the physical information includes at least one of information about an eggshell temperature and information about an egg weight.

5. The chick production method according to claim 1, wherein the first characteristic is a first expected hatching time of the first live group and the second characteristic is a second expected hatching time of the second live group.

6. The chick production method according to claim 1, wherein the mid-hatch eggs of the first live group are expected to hatch earlier than the mid-hatch eggs of the second live group.

7. The chick production method according to claim 1, wherein the physical information is selected from the group consisting of an egg weight, an eggshell temperature, an ovoid coefficient, an air chamber height, an air chamber volume, an eggshell thickness, an eggshell strength, fetal movement, and a heartbeat of an embryo.

8. The chick production method according to claim 1, wherein, after dividing the mid-hatch eggs into the plurality of groups, transferring eggs of the first live group to a first part of the hatcher and eggs of the second live group to a second part of the hatcher, without transferring non-live eggs of the non-live group to either the first or second parts of the hatcher.

9. A chick production system comprising:
a measurement device configured to measure physical information about mid-hatch eggs accommodated in a setter tray or about the mid-hatch eggs taken out from the setter tray;
a sorter configured to divide the mid-hatch eggs into a plurality of groups based on the physical information measured by the measurement device; and
a hatcher configured to accommodate the mid-hatch eggs in a plurality of hatcher trays for each of the groups divided by the sorter,
wherein chicks are developed from the mid-hatch eggs in each of the plurality of the hatcher trays,
wherein the plurality of groups include a first live group, a second live group, and a non-live group, wherein the first live group has a first characteristic different from a second characteristic of the second live group, and
wherein the hatcher is configured to perform different temperature control for the first live group and for the second live group.

10. The chick production system according to claim 9, wherein, after the mid-hatch eggs are divided into the plurality of groups, the hatcher is configured to transfer eggs of the first live group to a first part of the hatcher and eggs of the second live group to a second part of the hatcher, without transferring non-live eggs of the non-live group to either the first or second parts of the hatcher.

11. A chick production method comprising:
measuring, by a measuring device, physical information about mid-hatch eggs during a period from when the mid-hatch eggs are accommodated in a setter tray to when the mid-hatch eggs are transferred to a hatcher tray;
dividing, by a sorter, the mid-hatch eggs into a plurality of live groups based on the measured physical information to accommodate the mid-hatch eggs in the hatcher tray;
wherein, in the dividing the mid-hatch eggs into the plurality of live groups to accommodate the mid-hatch eggs in the hatcher tray, attribute information about the mid-hatch eggs is used in addition to the physical information about the mid-hatch eggs, and
the attribute information is selected from the group consisting of a chicken species, age of a parent chicken, a laying date and time, a content of feed, a medical history and a vaccination history of the parent chicken; and
adjusting, by a hatcher, temperature of the mid-hatch eggs accommodated in the hatcher tray to develop chicks.

12. The chick production method according to claim 11, wherein the physical information is selected from the group consisting of an egg weight, an eggshell temperature, an ovoid coefficient, an air chamber height, an air chamber volume, an eggshell thickness, an eggshell strength, fetal movement, and a heartbeat of an embryo.

* * * * *